(12) United States Patent
Bauer et al.

(10) Patent No.: US 8,073,636 B2
(45) Date of Patent: Dec. 6, 2011

(54) METHOD AND DEVICE FOR DETERMINING THE COMPOSITION OF A GAS MIXTURE OF A FUEL TANK OF A MOTOR VEHICLE FILLED WITH CNG

(75) Inventors: Erwin Bauer, Lappersdorf (DE); Dietmar Ellmer, Regensburg (DE)

(73) Assignee: Continental Automotive GmbH, Hannover (DE)

( * ) Notice: Subject to any disclaimer, the term of this patent is extended or adjusted under 35 U.S.C. 154(b) by 160 days.

(21) Appl. No.: 12/162,038

(22) PCT Filed: Mar. 1, 2007

(86) PCT No.: PCT/EP2007/051959
§ 371 (c)(1),
(2), (4) Date: Jul. 24, 2008

(87) PCT Pub. No.: WO2007/131814
PCT Pub. Date: Nov. 22, 2007

(65) Prior Publication Data
US 2009/0088983 A1 Apr. 2, 2009

(30) Foreign Application Priority Data
May 12, 2006 (DE) .......................... 10 2006 022 357

(51) Int. Cl.
*G01N 33/22* (2006.01)
*G06F 17/40* (2006.01)
(52) U.S. Cl. ................. 702/24; 702/22; 702/30; 702/32

(58) Field of Classification Search .................... 702/24, 702/22, 27, 30, 32, 140
See application file for complete search history.

(56) References Cited

U.S. PATENT DOCUMENTS

| 4,370,150 | A | * | 1/1983 | Fenstermaker | .................... 95/49 |
| 5,542,392 | A | | 8/1996 | Povinger | .................... 123/480 |
| 5,697,346 | A | * | 12/1997 | Beck | .................... 123/494 |
| 5,900,515 | A | * | 5/1999 | Mallinson et al. | .................... 585/6 |

FOREIGN PATENT DOCUMENTS

| DE | 44 46 081 A1 | 6/1995 |
| EP | 0 894 959 A | 2/1999 |
| WO | WO 94/24433 A | 10/1994 |

OTHER PUBLICATIONS

Translation of EP0894959, translated Jul. 20, 2010.*

* cited by examiner

*Primary Examiner* — Hal Wachsman
(74) *Attorney, Agent, or Firm* — King & Spalding L.L.P.

(57) ABSTRACT

Systems and methods for determining the gas composition of a gas mixture in a fuel tank of a motor vehicle filled with a compressed natural gas (CNG) mixture are provided. A pressure sensor and a temperature sensor are used to measure a gas pressure and a gas temperature in the fuel tank A processor may execute an algorithm to determine, based at least on the measured gas temperature and the measured gas pressure in the fuel tank, a current vapor pressure of each of at least one component of the CNG mixture in the fuel tank. If the measured gas pressure in the fuel tank falls below a threshold, a corresponding current composition of the CNG mixture in the fuel tank may be determined.

15 Claims, 4 Drawing Sheets

METHOD AND DEVICE FOR DETERMINING THE COMPOSITION OF A GAS MIXTURE OF A FUEL TANK OF A MOTOR VEHICLE FILLED WITH CNG

CROSS-REFERENCE TO RELATED APPLICATIONS

This application is a U.S. national stage application of International Application No. PCT/EP2007/051959 filed Mar. 1, 2007, which designates the United States of America, and claims priority to German application number 10 2006 022 357.8 filed May 12, 2006, the contents of which are hereby incorporated by reference in their entirety.

TECHNICAL FIELD

The invention relates to a method or a device for determining the gas composition of a fuel tank of a motor vehicle filled with a CNG mixture.

BACKGROUND

It is already known that motor vehicles equipped with an Otto engine can be operated with a natural gas, known as CNG (Compressed Natural Gas). The CNG mixture is also known as natural gas. With the appropriate equipment, such a CNG motor vehicle can be operated either exclusively with natural gas (monovalent operation) or as a bi-fuel variant with the option of gasoline or natural gas operation. The natural gas is heavily compressed at high pressure of around 200 bar and fed into one or more pressurized fuel tanks in the motor vehicle. The main component of natural gas is methane ($CH_4$) with 85-98%. In addition however natural gas also contains significant proportions of higher hydrocarbons such as ethane ($C_2H_6$), propane ($C_3H_8$) and butane ($C_4H_{10}$). This is then referred to as a wet natural gas. The reason for this lies in the fact that the ethane, propane and butane components have a relatively low vapor pressure and thus vaporize quickly under pressure. The vapor pressure at 20° C. amounts to around 38 bar for ethane, 8.5 bar for propane and 2.0 bar for butane. Methane, the main component of the natural gas, only has a vapor pressure of 1.47 bar at a temperature of minus 157° C.

If the fuel tank is filled with the CNG mixture at high pressure, it is essentially methane that is available in a gaseous form, with the ethane, propane and butane components mostly being present in a liquid phase. These liquid components collect on the floor of the fuel tank and are not used while the gas pressure in the fuel tank is greater than the vapor pressure of ethane, propane or butane. If on the other hand the gas pressure in the fuel tank reaches the value of the vapor pressure of ethane, then the liquid ethane proportion evaporates first, for which the vapor pressure at 20° C. lies at around 38 bar. If the gas pressure in the fuel tank falls further, then at 8.5 bar the propane proportion and finally at 2 bar the butane proportion evaporate. The result of this physical behavior is that when the gas mixture is injected into the internal combustion engine in conjunction with the induced air, the chemical composition of the gas mixture changes continuously. With a full fuel tank a pure methane-air mixture is injected or burned, with the gas pressure in the fuel tank (system pressure) falling continuously. When the vapor pressure of ethane is reached at around 38 bar, this begins to evaporate and a mixture of methane and ethane is produced. The system pressure remains constant until such time as the ethane proportion in the fuel tank is evaporated. Subsequently the system pressure falls further. When the system pressure reaches the vaporization threshold of propane at around 8.5 bar. the liquid propane proportion evaporates. As from this point a fuel mixture of methane, ethane and propane is burned.

As the tank is emptied further, the butane proportion also evaporates at appr. 2 bar. In practice the latter situation will hardly ever occur since as a rule the injection pressure in the cylinder of the internal combustion engine is driven to over 2 bar and thus the butane proportion remains liquid and in such cases accumulates continuously in the fuel tank.

Since the different components of the CNG have different energy contents, significant effects emerge for the operating behavior of the internal combustion engine in relation to the cylinder filling, the mixture formation, the duration of the fuel injection and the combustion. The exhaust gas emissions can also be especially influenced by this.

SUMMARY

The gas injection into the combustion chamber of an internal combustion engine can be improved, taking into account the current composition of the CNG in the fuel tank. According to an embodiment, a method for determining the gas composition of a fuel tank of a motor vehicle filled with a CNG mixture, may comprise the steps of permanently measuring the gas pressure and the gas temperature in the fuel tank of the motor vehicle, wherein an algorithm is used to determine from the measured temperature and the measured gas pressure in the fuel tank the current vapor pressure of at least one component of the CNG mixture, especially for methane, ethane, propane and/or butane, and if the gas pressure of one of the components of the CNG mixture in the fuel tank falls below a threshold, a corresponding current composition of the gas mixture is determined.

According to a further embodiment, the current vapor pressure of a component of the CNG can be taken from a stored table or pressure curve. According to a further embodiment, on further withdrawal of gas packages, the start of evaporation of one of the components of the CNG can be taken from the horizontal pressure characteristic of the stored pressure curve. According to a further embodiment, the computation of the gaseous methane amount ($m_{methane}$) can be calculated immediately before the evaporation of ethane according to the formula $$m_{methane} = p_d * V / (R_{methane} * T),$$

with $p_d$ being the vapor pressure, V the gas volume, $R_{methane}$ a gas constant and T the gas temperature in the fuel tank. According to a further embodiment, the vapor pressure $p_d$ can be calculated according to the formula $$p_{dethane} = \rho_{ethane} * R_{ethane} * T,$$

with T being the gas temperature in the fuel tank, R a gas constant and ρ the gas density. According to a further embodiment, a mixed gas constant $$R_{Mix} = (m_{ethane} * R_{methane} + m_{ethane} * R_{ethane})(m_{methane} + m_{ethane})$$

can be computed for further gas packages of methane and ethane withdrawn. According to a further embodiment, the gas volume V in the fuel tank can be computed according to the formula $$V = (\Delta m_{methane} * R_{methane})(P_1/T_1 - P_2/T_2)$$

According to a further embodiment, the measured vapor pressure can be compared with the computed required value. According to a further embodiment, the amount of gas to be injected for the internal combustion engine of the motor vehicle can be adapted depending on the current gas composition. According to a further embodiment, the amount of gas to be injected into an internal combustion engine, can be adapted taking into account the current gas composition in the fuel tank and/or its energy value in relation to a modelled consumption behavior of the internal combustion engine. According to a further embodiment, the duration of the injection and/or the ignition angle can be adapted. According to a further embodiment, the ignition angle can be adapted to current operating conditions of the internal combustion engine, especially in the start phase, while the engine is warming up and/or during lean-burn operation. According to a further embodiment, a calculation can be made to check the volume, in which case, assuming a known amount of methane gas, a fall in pressure in the fuel tank is measured, from which the specified tank volume can be deduced. According to a further embodiment, with a parked motor vehicle if ambient conditions change, especially the temperature and/or the gas pressure in the fuel tank a new composition of the gas mixture can be computed and the new composition of the gas mixture can accordingly be taken into consideration when the engine is started again.

According to another embodiment, a device for determining the composition of the gas mixture of a fuel tank filled with a CNG mixture, may comprise a program-controlled processing unit, wherein the processing unit is operable to determine the gas composition with the aid of an algorithm and using a measured temperature and gas pressure in the fuel tank.

According to a further embodiment, the processing unit may be part of an engine management device present in the motor vehicle.

BRIEF DESCRIPTION OF THE DRAWINGS

An exemplary embodiment of the invention is shown in the drawing and will be explained in greater detail in the description given below.

DETAILED DESCRIPTION

The method for determining the gas composition or the device according to various embodiments may have the advantage that, independently of the prevailing gas pressure (system pressure) in the fuel tank, a gas mixture is always made available which, with a current engine requirement, corresponds to the specified setpoint value. This enables not only the power curve of the internal combustion engine to be improved, but in particular the exhaust gas emission to be optimized as well. This is especially achieved in that, with the aid of an algorithm, the current vapor pressure of at least one component of the CNG mixture, especially for ethane, propane and/or butane, is able to be determined. When the vapor pressure of one of the components falls below a lower threshold a corresponding current composition of the gas mixture is established.

It is viewed as especially advantageous that the current vapor pressure of a component of the CNG can be taken very easily from a previously stored table or pressure curve. Since the temperature and the gas pressure in the fuel tank are measured continuously, with further ongoing gas removal the current vapor pressure of ethane for example can be taken from the horizontal curve part of the stored pressure curve.

Also useful is the fact that the gaseous methane amount, which is withdrawn immediately before the evaporation of ethane, can be computed with a very simple formula.

The vapor pressure can be computed with a further formula if the gas temperature in the fuel tank, the gas constant and the gas density are known.

An important variable is the knowledge of the gas volume in the fuel tank. Furthermore a very simple formula allows the volume to be checked. Then a drop in pressure occurs in the fuel tank when a known amount of methane fuel is withdrawn.

To validate measurement and computation there is provision for the measured vapor pressure (actual value) to be compared with the computed setpoint value. An error can be identified very easily in this way.

Another advantage of the various embodiments can also be seen in that the amount of gas to be injected for the internal combustion engine of the motor vehicle is adapted as a function of the current gas composition. In particular this allows energetic differences of the gas components to be compensated for. It is also viewed as especially advantageous that the amount of gas to be injected is adapted taking into account its energy content in relation to the modelled fuel consumption behavior of the internal combustion engine. This adaption can for example be made by the adjustment of the ignition angle and/or alternately by changing the injection duration and thus the amount of fuel injected. In particular these adaptations can be performed for example in the start phase, when the engine is warming up and/or during lean-burn operation.

A very advantageous solution is also seen in the fact that, when a motor vehicle is parked, a new value is computed for the gas composition, especially if the ambient conditions, above all the temperature and/or the gas pressure in the fuel tank, have changed. The newly determined gas composition is then taken into account accordingly when the engine is next started.

Finally the various embodiments also may have the advantage that the device for determining the gas composition features a program-controlled processing unit. With this processing unit, with the aid of an algorithm and using the temperature and the gas pressure measured in the fuel tank, the gas composition can be determined very easily and without any great computing effort. In such cases it has proved to be particularly advantageous for the processing unit to be integrated into an engine control device which is already present in the motor vehicle. The available engine control unit merely needs an appropriate software program with which the methods according to various embodiments can be realized.

Figure 1:
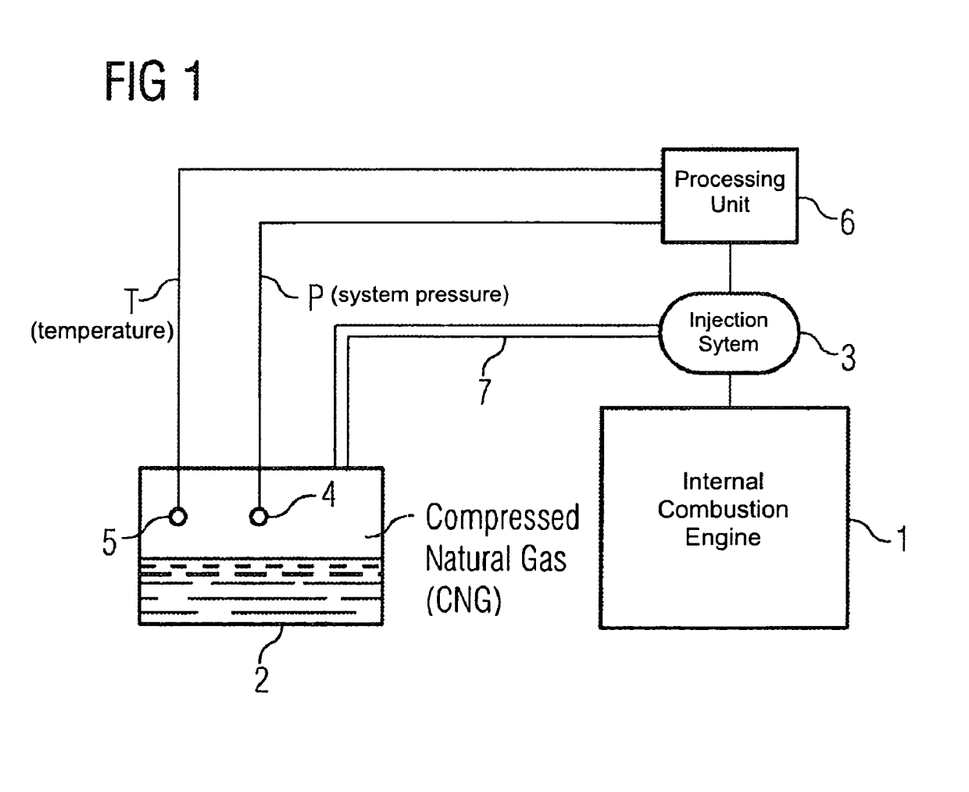
FIG. 1 shows a block diagram of a device according to an embodiment for determining the gas composition.

The block diagram of FIG. 1 shows an exemplary embodiment, in which an internal combustion engine 1 is connected to an injection system 3. The internal combustion engine 1 is embodied as an Otto engine. The Otto engine in such cases can be embodied monovalent for combustion of the CNG or in bivalent operation for switching between gasoline injection or gas injection. The gas is injected by means of the injection system 3. The injection system 3 is connected via a hydraulic line 7 to a fuel tank 2 in which the CNG mixture is stored. The fuel tank 2 is a embodied to resist high pressure so that it withstands the usual filling pressure of up to 200 bar. Because of the high gas pressure the CNG mixture is partly stored in the liquid state. The CNG mixture contains 85-98% Methane as its main component, which because of a vapor pressure is present in gaseous form. The components ethane, propane and butane exhibit a significantly lower vapor pressure so that these proportions are stored in liquid form in the fuel tank 2.

Furthermore a pressure sensor 4 and also a temperature sensor are arranged in or on the tank. These sensors 4, 5 continuously measure the temperature T as well as the gas pressure (system pressure) P within the fuel tank 2. The measured values are transferred via corresponding electrical lines to a processing unit 6. As a result of the data received the processing unit 6 computes a current composition of the gas within the fuel tank 2 or the gas system, with the aid of an appropriate algorithm which will be explained in greater detail below. The processing unit 6 essentially has a control program with which the various parameters, for example the vapor pressure of a component of the CNG mixture, the tank volume, the gas composition etc. are calculated.

In an alternate embodiment the processing unit 6 is integrated into an engine control device which is present in any event for control of the internal combustion engine.

Figure 2:
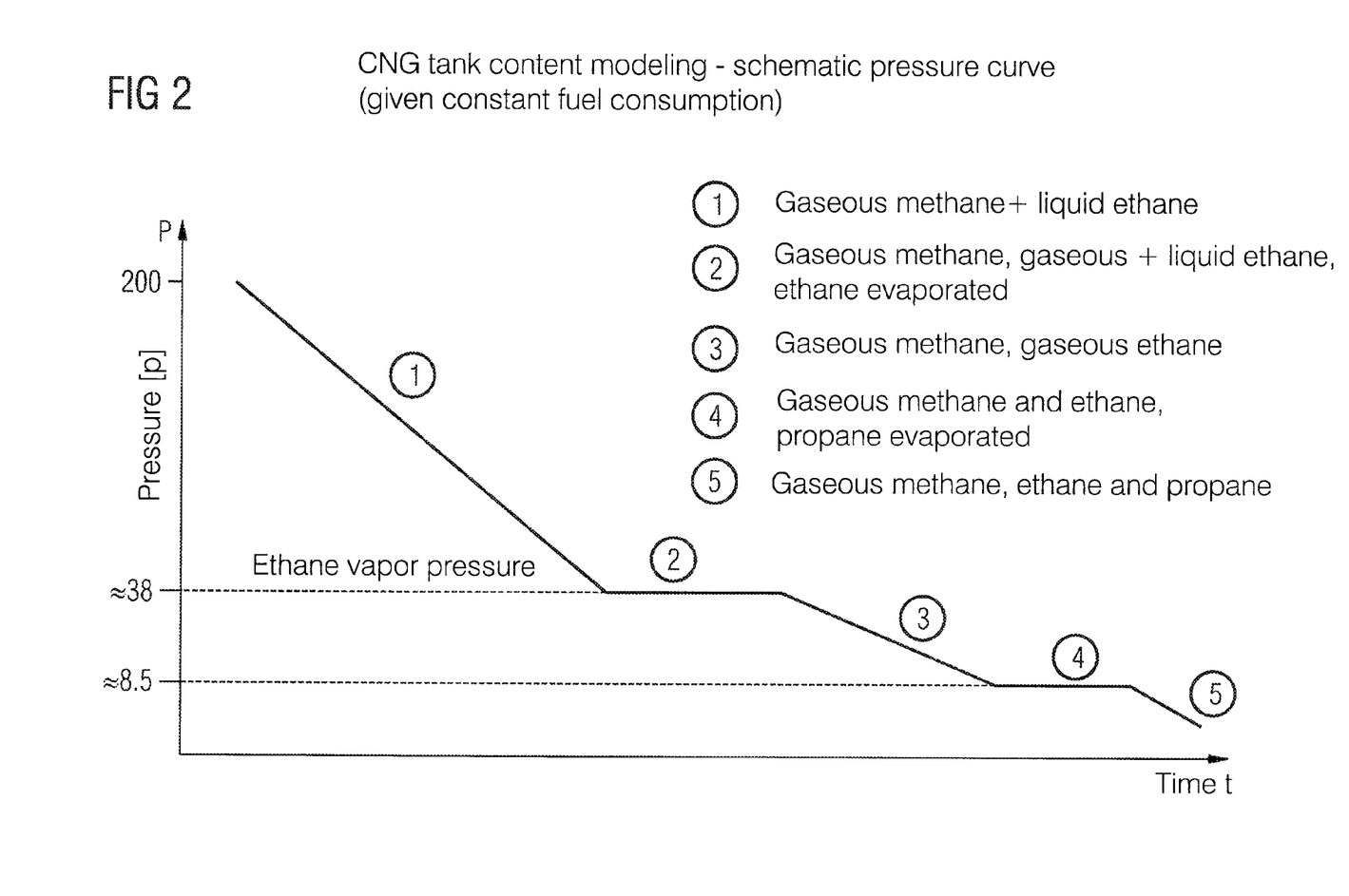
FIG. 2 shows a first diagram of a plot indicating pressure in a fuel tank versus time.

The functioning of this arrangement is explained in greater detail with reference to the first diagram of FIG. 2. The diagram shows a pressure curve on which the gas pressure p in the fuel tank, as measured by the pressure sensor 4, is plotted on the Y axis. The timing of the gas pressure p which is measured by the pressure sensor 4 is plotted on the X axis. The fuel tank in this case is filled with the CNG mixture, with the CNG mixture, in addition to methane, also including the components ethane, propane and butane. It is assumed that the fuel tank is filled at a gas pressure of 200 bar. The pressure curve shown in FIG. 2 shows an example of the ratio between the components methane, ethane and propane. The pressure curve would continue in a similar manner for the butane proportion.

With the aid of the available pressure and temperature sensors the gas temperature and the gas pressure are measured continuously in the fuel tank. Simultaneously the vapor pressure of ethane is computed in the processing unit. The computation of the vapor pressure of ethane can alternatively also be determined from the pressure curve shown in FIG. 2, since the time at which the evaporation of the ethane proportion begins can be taken from the point at which it reaches the vapor pressure value at around 38 bar. This part corresponds to the part of the curve 2 running horizontally. The falling part of the curve 1, which runs between at the pressure values of 200 and 38 bar, by contrast specifies that in this pressure range only the methane gas is present since the other components of the gas mixture are present in their liquid phase in the range below 38 bar On reaching the gas pressure or 38 bar ethane begins to evaporate so that, despite the further removal of gas, the gas pressure in the fuel tank does not fall any further but also does not rise. This can be seen from the fact that the curve runs horizontally 2. Since the pressure in the fuel tank generally drops very slowly this point of the part of the curve 2 can be determined more simply and more precisely if knowledge of the vapor pressure is available. On the other hand the vapor pressure value determined from the curve shape can conversely be compared to the calculated value in order especially to check the measurement accuracy and thereby exclude a possible error. This allows the system security to be increased in an advantageous manner.

The vapor pressure is defined by the following formula $$p_d = \rho * R * T$$

with $p_d$ being the vapor pressure, $\rho$ the gas density, R a gas constant and T the gas temperature.

If the case now arises in which the fuel tank is emptied far enough for the pressure to fall below the vapor pressure $p_d$=38 bar of ethane, the processing unit or the engine management device reacts. The tank content at this point in time comprises the remaining gaseous components and the amount of liquid ethane collected in the past. At this vapor pressure of $p_d \approx 38$ bar ethane evaporates, so that the engine now burns a gas mixture of methane, ethane and air, with its energy content differing from that obtaining when pure methane combustion is taking place. The amount of gas to be brought into the cylinder must be adapted according to the current gas mixture quality to cater for the changed chemical composition of the fuel (X % methane, Y % ethane) and to maintain the defined air-fuel ratio. The composition of the gas mixture and thus the injection amount to be set by the engine management device changes continuously. The change occurs until such time as the entire ethane proportion has evaporated. As well as the adaptation of the injection amount, further adaptations are undertaken especially when the internal combustion engine is started, while it is warming up and above all during lean-burn operation. In particular the ignition angle can be adjusted and/or the duration of the injection can be adapted in accordance with the energy content or the calorific value of the gas mixture. Furthermore the modelled injection behavior of the engine is to be corrected in accordance with the current composition of the gas mixture.

While ethane is evaporating, the system is balanced and the tank pressure remains constant, as can be seen from curve part 2 of FIG. 2. Only when the entire ethane proportion is evaporated does the tank pressure continue to fall further in accordance with curve part 3.

The computation of the composition of the gas mixture for the period in which methane and ethane are present in their gaseous state is explained in greater detail below.

As can also be seen from FIG. 2, the evaporation of the gas components for propane occurs in a similar way to the way previously described for ethane. If the tank pressure falls to around 8.5 bar, the liquid propane proportion then evaporates so that the pressure in the fuel tank remains constant in accordance with curve part 4. Only if the entire propane proportion has evaporated and gas continues to be withdrawn does the gas pressure in the fuel tank continue to fall in accordance with curve part 5.

A particular situation can arise if the vehicle is parked and if the ambient conditions, especially the temperature and the pressure conditions in the fuel tank, change while the vehicle is standing. Changes in temperature can for example cause the gas pressure in the fuel tank to become greater than the vapor pressure of a gas proportion. If the temperature falls the gas pressure can become less or constant with the vapor pressure. There is provision for these special cases for the amount of ethane or propane in vapor form to be recalculated. When the engine is started again the new composition of the gas mixture is then used as a basis.

Figure 3:
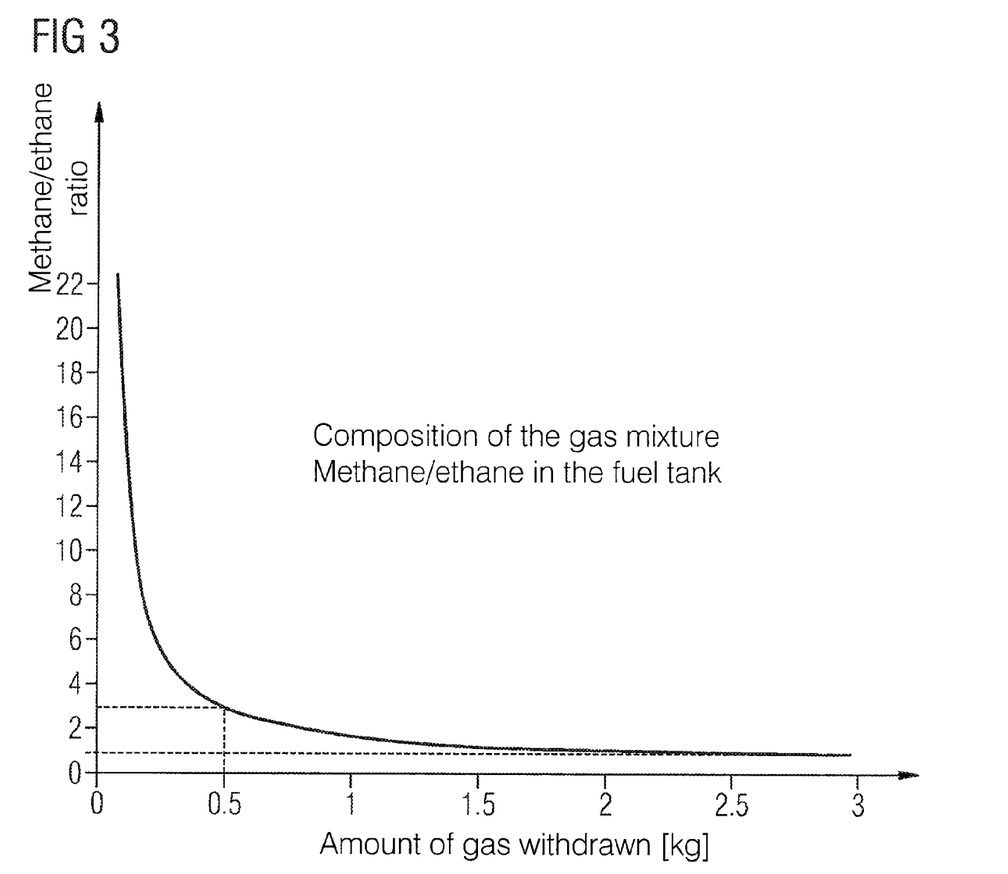
FIG. 3 shows a second diagram of a plot indicating the methane/ethane ratio versus the amount of gas removed from the fuel tank.

In the other diagram of FIG. 3 the ratio between methane and ethane is shown on the Y axis. The amount of gas removed in kg is plotted on the X axis. It is evident from the falling branch of the methane/ethane curve that at higher gas pressure and smaller amount of gas removed the methane proportion in the gas mixture is up to 22 times greater than the ethane proportion. When only around 0.5 kg of the gas mixture is removed the methane proportion is only around three times as high as the ethane proportion. The methane proportion falls further so that for a mass of gas of around 3 kg removed, the ratio of methane to ethane is around 1:1. Based on this curve shape it is clear that the injection conditions for the internal combustion engine are continuously to be adapted to the current gas composition in the fuel tank.

The computation of the current gas mixture composition in the fuel tank is explained in greater detail below using a methane and ethane as an example. The amount of methane in the fuel tank at the point in time directly before the evaporation of methane, i.e. at the beginning of the horizontal curve part 2 (FIG. 2) is computed with the following formula $$m_{methane} = p_d * V / (R_{methane} * T)$$

It is assumed that an amount of gas $\Delta m$ is withdrawn in one working cycle. The amount of gas $\Delta m$ to be withdrawn is assumed to be known. For example the value of $\Delta m$ is determined from the mass of air sucked in and the corresponding $\lambda$ value. The first gas to be withdrawn from the fuel tank is pure methane gas. The continuous withdrawal of gas finally causes the tank pressure to fall below the vapor pressure of ethane (appr. 38 bar). This causes as much ethane to evaporate as to reach the vapor pressure again.

The formula for calculating the first evaporated amount of ethane is as follows:

$$m_{ethane} = \Delta m * R_{methane} / R_{ethane}$$

The further gas packages withdrawn contain both methane and also ethane. Thus a mixed gas constant $R_{Mix}$ is to be used, which corresponds to the composition of the gas mixture. The mixed gas constant $R_{Mix}$ is recalculated for each working cycle in accordance with the following formula $$R_{Mix} = (m_{methane} * R_{methane} + m_{ethane} * R_{ethane}) / (m_{methane} + M_{ethane})$$

Each further evaporated ethane amount is calculated in accordance with the following formula $$m_{ethane} = \Delta m * R_{Mix} / R_{ethane}$$

The actual partial pressure p of ethane is calculated according to the formula $$p_{ethane} = m_{ethane} * R_{ethane} * T / V,$$

with V being the current tank volume.

The current partial pressure p of methane is calculated in accordance with the following formula $$p_{methane} = P_d P_{ethane}$$

Furthermore the amount or a ethane currently present is calculated in accordance with the formula $$m_{ethane} = (P_{ethane} * V)(R_{ethane} * T)$$

The next gas package $\Delta m$ withdrawn is composed of methane and ethane. In this case an ideal mixing of the gas is used as the starting point so that the gas package $\Delta m$ can be calculated as follows:

$$\Delta m - \Delta m_{methane} + \Delta m_{ethane}$$

$$\Delta m_{methane} - \Delta m * S / (1+S)$$

$$\Delta m_{ethane} = \Delta m * (1 - S/(1+S))$$

This produces the current gas composition S in accordance with the formula $$S_{current} = \frac{m_{methane,current}}{m_{ethane,current1}}$$

$$= \frac{m_{methane,old} - \frac{S_{alt}}{1 - S_{alt}} - \Delta m_{current}}{m_{ethane,old} - \left(1 - \frac{S_{old}}{1 + S_{old}}\right) \cdot \Delta m_{current} + \frac{R_{Mix,current}}{R_{ethane,current}} \cdot \Delta m_{current1}}$$

By using at the previously calculated parameter values.

The calculation of the mixture composition is undertaken iteratively and is recalculated for each working cycle in which a gas mixture is withdrawn and a specific ethane proportion is evaporated.

The evaporation of liquid ethane means that the volume of the tank increases slightly and does so by precisely the proportion that ethane occupies in its liquid form. The factor $\rho$ is the density of the liquid ethane (0.54 kg/l). This produces a change in volume $\Delta V$ $$\Delta V = \Delta m_{ethane} \cdot \rho_{ethane}$$

The current tank volume V is once again computed for each working cycle. This produces the following result $$V = V_{old} + \Delta V$$

An alternate calculation method is explained below. The alternate calculation method is physically equivalent to the calculation method mentioned previously. It has the advantage however that with this calculation method the processing unit can be presented in a structurally simpler way. In this alternate calculation method the current gaseous components of methane, mmethane and ethane methane are administered separately. The ratio X of the respective proportion to the overall amount of vapor is formed.

$$X_{methane} = \frac{m_{methane}}{m_{methane} + m_{ethane}}$$

$$X_{ethane} = 1 - X_{methan}$$

The amount of gas injected per working cycle m is then made up as follows:

$$\Delta m_{methane} = X_{methane} \cdot \Delta m$$

$$\Delta m_{ethane} = X_{ethane} \cdot \Delta m$$

The respective proportions $\Delta m_{methane}$ and $\Delta m_{ethane}$ are then derived from the last $\Delta m_{methane}$ and $\Delta m_{ethane}$ values determined. This produces the following current amounts for methane and ethane:

$$m_{methane,current} = m_{methane,old} - \Delta m_{methane}$$

$$m_{ethane,current} = m_{ethane,old} - \Delta m_{ethane} + \Delta m_{ethane,evaporated}$$

The amount of methane evaporating in a working cycle is then determined in a similar manner to that described previously.

If the gas pressure in the fuel tank falls below the vapor pressure of propane, propane evaporates and a fuel mixture of methane, ethane and propane is produced, as has previously been explained for FIG. 2 (curve parts 4 and 5). In this case the above formulae can be used in a similar manner. The only difference arising is that initially a fixed $R_{Mix}$ for the constant mass ratio of methane to ethane has to be calculated. For the rest of the calculation, instead of the values of methane, those of the mixed gas methane/ethane and instead of the value for ethane, that of propane is to be used.

Particular account should be taken of special cases which arise if the vehicle is parked and the external conditions, especially the ambient temperature and thereby the conditions in the tank change. A distinction is made between the following cases.

Case 1:

The temperature rises so far that ethane (or propane) which has already evaporated liquefies again. The gas pressure p is then greater than vapor pressure $p_d$.

In this case pure methane is present in the gaseous state. The proportion of ethane is zero. The calculation is undertaken in the manner already described above.

Case 2:

The temperature has dropped so far that the entire proportion of ethane is evaporated. In this case the gas pressure p is smaller than the vapor pressure $p_d$. The proportion of ethane is determined in this case as follows:

$$m_{ethane} = \left(\frac{p \cdot V}{T} - m_{ethane} \cdot R_{methane}\right) / R_{ethane}$$

Case 3:

The temperature has risen or fallen so far that the vapor pressure currently predominates ($p=p_d$). This is merely a special case of case 2 and is treated exactly like case 2.

The way in which the volume of the tank is determined is explained below.

The tank volume is an important variable in the formulae given above. Depending on how large the proportion of liquid in gas components is, the value can vary. The volume is determined as follows. In the phase in which only methane is present in gaseous form, a specific amount $\Delta m_{methane}$ is burned. The amount $\Delta m_{methane}$ is known to the processing unit and can be calculated for example from the amount of air sucked in and the $\lambda$ number. The withdrawal of the amount of fuel leads to a fall in pressure in the tank $\Delta p=p_1-p_2$. The tank volume can be computed from this. If the gas temperature changes while the fuel is being withdrawn, this change is also taken into account in accordance with the following formula:

$$V = \frac{\Delta m_{methane} \cdot R_{methane}}{\frac{P_1}{T_1} - \frac{P_2}{T_2}}$$

Figure 4:
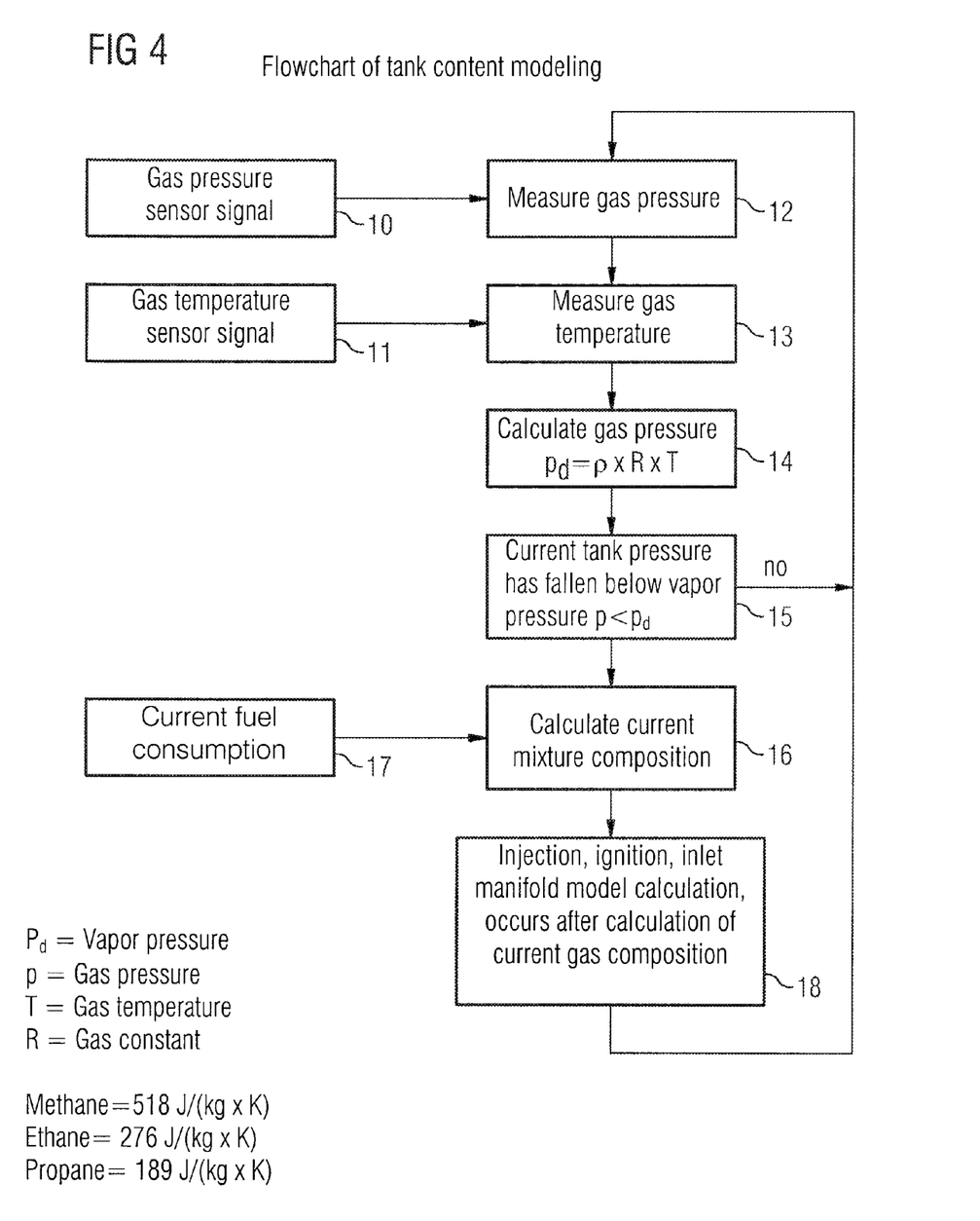
FIG. 4 shows a flowchart for the device for modeling the contents of a fuel tank, according to an embodiment of the invention.

The flow diagram of FIG. 4 shows a flowchart for modeling the tank content. Initially, in box 10 and 11 the gas pressure in the fuel tank or the temperature in the fuel tank is determined with the aid of built-in sensors. The gas pressure or the gas temperature is then available in boxes 12 and 13 and is buffered. Subsequently, in box 14 the vapor pressure is computed in accordance with the following formula $$P_d = \rho*R*T$$

which has been explained previously.

A check is performed in box 15 as to whether the current gas pressure in the fuel tank is less than the vapor pressure of a gas element. If it is not, the program returns to box 12 and the cycle is repeated. Otherwise, if the gas pressure in the fuel tank is less than the vapor pressure, the composition of the gas mixture is then computed in box 16. Furthermore, in box 17 a current fuel consumption is computed and this value is taken into account when computing the composition of the gas mixture. Subsequently, in box 18, depending on the current composition of the gas mixture, the injection is corrected accordingly.

This correction can for example be made by adjusting the ignition, especially the ignition angle, by changing the injection duration, by an induction manifold model calculation and/or suchlike. After this correction the program jumps back to box 12 and the cycle is repeated once again.

LIST OF REFERENCE SYMBOLS

1 internal combustion engine
2 Fuel tank
3 Injection system
4 Pressure sensor
5 Temperature sensor
6 Processing unit/device
7 Hydraulic line
10 . . . 18 Boxes in the flowchart
m Gas amount (mass)
p Gas pressure
$p_d$ Vapor pressure
T Gas temperature (in the fuel tank)
t Time axis

The invention claimed is:

1. A method for determining the gas composition of a gas mixture in a fuel tank of a motor vehicle filled with a compressed natural gas (CNG) mixture, comprising the steps of:
   using a pressure sensor to measure a gas pressure and using a temperature sensor to measure a gas temperature in the fuel tank of the motor vehicle;
   using a processor embodied in hardware to:
      execute an algorithm that relates temperature with vapor pressure to calculate a current vapor pressure of a particular component of the CNG mixture in the fuel tank based on the measured temperature in the fuel tank, the vapor pressure of the particular component of the CNG mixture being defined as the pressure at which the particular component changes state from a liquid to a gas;
      compare the measured as pressure in the fuel tank with the determined vapor pressure for the component of the CNG mixture; and
      if the measured gas pressure in the fuel tank falls below the determined vapor pressure for the particular component of the CNG mixture, determining a current composition of the CNG mixture in the fuel tank.

2. The method according to claim 1, further comprising:
   determining a predetermined value for the current vapor pressure of the particular component of the CNG mixture from a stored table or pressure curve; and
   comparing the predetermined value for the current vapor pressure for the particular CNG component with the current vapor pressure for the particular CNG component determined using the algorithm.

3. The method according to claim 1, wherein:
   the particular component of the CNG mixture is gaseous methane; and
   the method further includes calculating an amount of gaseous methane in the fuel tank, wherein the computation of the gaseous methane amount ($m_{methane}$) is calculated according to the formula $$m_{methane}=p_d*V/(R_{methane}*T),$$

with $p_d$ being the current vapor pressure of the gaseous methane determined using the algorithm, V being a calculated gas volume of gas in the fuel tank, $R_{methane}$ being a gas constant, and T being the measured gas temperature in the fuel tank.

4. The method according to claim 1, further comprising calculating the current vapor pressure for ethane ($p_d$) according to the formula $$p_{dethane}=\rho_{ethane}*R_{ethane}*T,$$

with T being the measured gas temperature in the fuel tank, R being a gas constant, and $\rho$ being a gas density of gas in the fuel tank.

5. The method according to claim 1, further comprising calculating a mixed gas constant according to the formula $$R_{Mix}=(m_{methane}*R_{methane}+m_{ethane}*R_{ethane})/(m_{methane}+m_{ethane}).$$

6. The method according to claim 1, further comprising calculating the gas volume V in the fuel tank according to the formula $$V=(\Delta m_{methane}*R_{methane})/(P_1/T_1-P_2/T_2).$$

7. The method according to claim 1, further comprising:
adapting an amount of gas to be injected into an internal combustion engine of the motor vehicle based on the determined current composition of the CNG mixture in the fuel tank.

8. The method according to claim 1, further comprising:
adapting an amount of gas to be injected into an internal combustion engine based on at least one of (a) the determined current composition of the CNG mixture in the fuel tank and (b) a modelled consumption behavior of the internal combustion engine.

9. The method according to claim 8, wherein adapting the amount of gas to be injected into the internal combustion engine comprises adapting a duration of an injection and/or an ignition angle.

10. The method according to claim 8, further comprising adapting an ignition angle to current operating conditions of the internal combustion engine while the engine is warming up or during a lean-burn operation.

11. The method according to claim 1, further comprising:
measuring a fall in pressure in the fuel tank; and
calculating a volume of gas in the fuel tank based on the measured fall in pressure.

12. A system for determining the composition of a compressed natural gas (CNG) mixture in a fuel tank, the system comprising:
a temperature sensor operable to measure a temperature in the fuel tank;
a pressure sensor operable to measure a gas pressure in the fuel tank; and
a program-controlled processing unit operable to:
execute an algorithm that relates temperature with vapor pressure to calculate a vapor pressure for a component of the CNG mixture based on the measured temperature in the fuel tank, the vapor pressure of the particular component of the CNG mixture being defined as the pressure at which the particular component changes state from a liquid to a gas;
compare the measured gas pressure in the fuel tank with the determined vapor pressure for the component of the CNG mixture; and
if the measured gas pressure in the fuel tank is less than the determined vapor pressure for the component of the CNG mixture, determine a current composition of the CNG mixture in the fuel tank.

13. The system according to claim 12, wherein the processing unit is part of an engine management device of a motor vehicle.

14. The system according to claim 12, wherein the processing unit is further operable to:
determine a current gas composition; and
determine an adapted amount of gas to be injected into an internal combustion engine based on at least one of the current gas composition in the fuel tank and a modelled consumption behavior of the internal combustion engine.

15. A method for determining the gas composition of a fuel tank of a motor vehicle filled with a compressed natural gas (CNG) mixture, comprising the steps of:
using a pressure sensor to measure a gas pressure and using a temperature sensor to measure a gas temperature in the fuel tank of the motor vehicle;
using a processor embodied in hardware to:
determine, using a look-up table or pressure curve, a current vapor pressure of a particular component of the CNG mixture in the fuel tank based on the measured temperature in the fuel tank, wherein the particular component of the CNG mixture includes at least one of methane, ethane, propane and butane, and wherein the vapor pressure of the particular component of the CNG mixture is defined as the pressure at which the particular component changes state from a liquid to a gas;
compare the measured gas pressure in the fuel tank with the determined vapor pressure for the component of the CNG mixture; and
if the measured gas pressure in the fuel tank falls below the determined vapor pressure for the particular component of the CNG mixture, determining a current composition of the CNG mixture in the fuel tank.

* * * * *